(12) United States Patent
Shakespeare et al.

(10) Patent No.: US 8,049,892 B2
(45) Date of Patent: Nov. 1, 2011

(54) APPARATUS AND METHOD FOR CAMERA-BASED COLOR MEASUREMENTS

(75) Inventors: Tarja T. Shakespeare, Savo (FI); John F. Shakespeare, Savo (FI)

(73) Assignee: Honeywell International Inc., Morristown, NJ (US)

( * ) Notice: Subject to any disclaimer, the term of this patent is extended or adjusted under 35 U.S.C. 154(b) by 354 days.

(21) Appl. No.: 12/017,469

(22) Filed: Jan. 22, 2008

(65) Prior Publication Data

US 2009/0185185 A1 Jul. 23, 2009

(51) Int. Cl.
*G01N 21/25* (2006.01)

(52) U.S. Cl. .......................... 356/406; 356/402; 356/416

(58) Field of Classification Search .................. 356/406, 356/416, 402
See application file for complete search history.

(56) References Cited

U.S. PATENT DOCUMENTS

| | | | |
|---|---|---|---|
| 3,787,206 A * | 1/1974 | Goffe | 430/34 |
| 4,006,358 A | 2/1977 | Howarth | |
| 4,288,691 A | 9/1981 | Horton | |
| 4,315,279 A * | 2/1982 | Kuwayama et al. | 348/275 |
| 4,376,946 A | 3/1983 | Kaminow et al. | |
| 4,439,038 A | 3/1984 | Mactaggart | |
| 4,565,444 A | 1/1986 | Mactaggart | |
| 4,592,043 A | 5/1986 | Williams | |
| 4,634,928 A | 1/1987 | Figueroa et al. | |
| 4,699,510 A | 10/1987 | Alguard | |
| 4,786,817 A | 11/1988 | Boissevain et al. | |
| 4,807,630 A | 2/1989 | Malinouskas | |
| 4,856,014 A | 8/1989 | Figueroa et al. | |
| 4,883,963 A | 11/1989 | Kemeny et al. | |
| 4,928,013 A | 5/1990 | Howarth et al. | |
| 5,015,099 A | 5/1991 | Nagai et al. | |
| 5,047,652 A | 9/1991 | Lisnyansky et al. | |
| 5,122,974 A | 6/1992 | Chance | |
| 5,137,364 A | 8/1992 | McCarthy | |

(Continued)

FOREIGN PATENT DOCUMENTS

DE 3148076 A1 6/1983

(Continued)

OTHER PUBLICATIONS

Robert L. Feller, "Comments on the Measurement of "Yellowness" in Pulp and Paper," The Book and Paper Group Annual, vol. Six 1987, The American Institute for Conservation, May 1987, 9 pages.

(Continued)

*Primary Examiner* — Tarifur Chowdhury
*Assistant Examiner* — Isiaka Akanbi
(74) *Attorney, Agent, or Firm* — Munck Carter, LLP

(57) ABSTRACT

A method includes receiving light from a material at a digital imaging device. The method also includes filtering the light into at least three spectral bands using a filter, where different regions of the filter pass different spectral bands. The method further includes measuring the light in each of the spectral bands and determining at least one color associated with the material using the measured light in the spectral bands. The different regions of the filter could include multiple masks (where each mask passes one of the spectral bands), different areas of a linear variable filter, and/or individual filters (where each individual filter passes one of the spectral bands). The digital imaging device could include a digital camera. The filter could be formed on a detector in the digital camera, and/or a component of the digital camera could be replaced with the filter.

22 Claims, 4 Drawing Sheets

U.S. PATENT DOCUMENTS

| | | | |
|---|---|---|---|
| 5,220,172 A | 6/1993 | Berthold et al. | |
| 5,235,192 A | 8/1993 | Chase et al. | |
| 5,272,518 A * | 12/1993 | Vincent | 356/405 |
| 5,313,187 A | 5/1994 | Choi et al. | |
| 5,338,361 A | 8/1994 | Anderson et al. | |
| 5,374,555 A | 12/1994 | Pokora et al. | |
| 5,400,258 A | 3/1995 | He | |
| 5,642,189 A | 6/1997 | Alguard | |
| 5,642,192 A | 6/1997 | Gordon et al. | |
| 5,717,605 A * | 2/1998 | Komiya et al. | 356/406 |
| 5,774,213 A | 6/1998 | Trebino et al. | |
| 5,793,486 A | 8/1998 | Gordon et al. | |
| 5,795,394 A | 8/1998 | Belotserkovsky et al. | |
| 5,821,536 A | 10/1998 | Pettit | |
| 5,933,243 A | 8/1999 | Hagen | |
| 5,963,333 A | 10/1999 | Walowit et al. | |
| 5,992,318 A | 11/1999 | DiBello et al. | |
| 6,058,201 A | 5/2000 | Sikes et al. | |
| 6,074,483 A | 6/2000 | Belotserkovsky et al. | |
| 6,215,962 B1 * | 4/2001 | Cooper | 396/225 |
| 6,252,663 B1 * | 6/2001 | Cooper | 356/416 |
| 6,263,291 B1 | 7/2001 | Shakespeare et al. | |
| 6,272,440 B1 | 8/2001 | Shakespeare et al. | |
| 6,466,839 B1 | 10/2002 | Heaven et al. | |
| 6,499,402 B1 | 12/2002 | Sikes et al. | |
| 6,556,305 B1 | 4/2003 | Aziz et al. | |
| 6,584,435 B2 | 6/2003 | Mestha et al. | |
| 6,603,551 B2 | 8/2003 | Mestha et al. | |
| 6,724,473 B2 | 4/2004 | Leong et al. | |
| 6,743,337 B1 | 6/2004 | Ischdonat | |
| 6,760,103 B2 | 7/2004 | Shakespeare et al. | |
| 6,763,322 B2 | 7/2004 | Potyrailo et al. | |
| 6,805,899 B2 | 10/2004 | MacHattie et al. | |
| 6,856,436 B2 | 2/2005 | Brukilacchio et al. | |
| 6,949,734 B2 | 9/2005 | Neff et al. | |
| 7,199,884 B2 | 4/2007 | Jasinski et al. | |
| 7,291,856 B2 | 11/2007 | Haran et al. | |
| 7,573,575 B2 * | 8/2009 | Shakespeare et al. | 356/402 |
| 7,675,620 B2 * | 3/2010 | Imura | 356/402 |
| 2002/0001066 A1 * | 1/2002 | Kobayashi | 353/31 |
| 2002/0140832 A1 * | 10/2002 | Summa | 348/273 |
| 2003/0058441 A1 | 3/2003 | Shakespeare et al. | |
| 2004/0119781 A1 | 6/2004 | Szumla | |
| 2004/0212804 A1 | 10/2004 | Neff et al. | |
| 2004/0260520 A1 | 12/2004 | Braendle et al. | |
| 2005/0065400 A1 | 3/2005 | Banik et al. | |
| 2006/0132796 A1 | 6/2006 | Haran | |
| 2006/0243931 A1 | 11/2006 | Haran et al. | |
| 2007/0139735 A1 | 6/2007 | Shakespeare et al. | |
| 2007/0144388 A1 | 6/2007 | Shakespeare et al. | |
| 2007/0153277 A1 | 7/2007 | Shakespeare et al. | |
| 2007/0153278 A1 | 7/2007 | Shakespeare et al. | |

FOREIGN PATENT DOCUMENTS

| | | |
|---|---|---|
| DE | 19515499 A1 | 10/1996 |
| EP | 0 319 158 A1 | 6/1989 |
| EP | 1437222 A1 | 7/2004 |
| EP | 1457335 A1 | 9/2004 |
| EP | 1 491 877 A1 | 12/2004 |
| WO | WO 84/00181 A1 | 1/1984 |
| WO | WO 03/037111 A1 | 5/2003 |

OTHER PUBLICATIONS

M. K. Ramasubramanian et al., "Optical Sensor for Noncontact Measurement of Lignin Content in High-Speed Moving Paper Surfaces," IEEE Sensors Journal, vol. 5, No. 5, Oct. 2005, pp. 1132-1139.

C. I. Thomson et al., "Excitation Energy Transfer in Lignin: Fluorescence of Kraft Residual Lignin," 2004, 1 page.

S. Katuscak et al., "The Effect of Paper Degradation on Uncertainty of Determination of Initial Lignin Content," 2006, 3, pp. 69-72.

D.P. Koullas et al., "Fluorescence Spectroscopy for the Characterisation of Lignocellulosics—An Overview of the Recent Research," National Technical University of Athens, Bioresource Technology Unit, 2004, 57 pages.

Bo Albinsson et al., "The Origin of Lignin Fluorescence," Journal of Molecular Structure 508 (1999), pp. 19-27.

Tarja Shakespeare et al., "Problems in Colour Measurement of Fluorescent Paper Grades", Analytica Chimica Acta 380 (1999), pp. 227-242.

Tarja Shakespeare et al., "Advanced Colour Control Through Reflectance Optimization", Proceedings 2nd EcoPaperTech Conference, Helsinki Finland, Jun. 1998, pp. 183-194.

Custom Optics, "Filter, Color Sensor", 2008 JDS Uniphase Corporation, 6 pages.

Stokman et al., "Color Measurement by Imaging Spectrometry", Computer Vision & Image Understanding, San Diego, CA, US, vol. 79, No. 2, Aug. 2000, pp. 236-249.

Wandell, "Color Measurement and Discrimination", Journal of the Optical Society of America, USA, vol. 2, No. 1, Jan. 1985, pp. 62-71.

Tarja T. Shakespeare et al., "Apparatus and Method for Measuring and/or Controlling Paper Pulp Properties", U.S. Appl. No. 12/017,092, filed Jan. 21, 2008.

Tarja T. Shakespeare et al., "Apparatus and Method for Measuring and/or Controlling Ultraviolet-Activated Materials in a Paper-Making Process", U.S. Appl. No. 12/017,497, filed Jan. 22, 2008.

* cited by examiner

APPARATUS AND METHOD FOR CAMERA-BASED COLOR MEASUREMENTS

TECHNICAL FIELD

This disclosure relates generally to measurement systems and more specifically to an apparatus and method for camera-based color measurements.

BACKGROUND

Many different production and processing systems are used to produce paper products and other items having various colors. For example, paper production systems are often used to produce sheets of paper having different colors. As another example, printing systems are often used to print color graphics or other color content on sheets of paper. As yet another example, plastic film production systems are often used to produce sheets of plastic having different colors. It is often necessary or desirable to monitor the colors of items being produced or processed, such as to ensure that the items' colors are within standard or other specifications.

Spectrophotometers and calorimeters are often used to measure surface or transmittance colors of still or moving items. Spectrophotometers often use spectrometers that are based on diffraction gratings, and these spectrometers often have a low optical throughput. This optical throughput can be increased using transmission gratings, but even then only one signal or channel can be analyzed at a time with a spectrometer. Moreover, spectrometers are often quite expensive and large in size. Colorimeters typically utilize photodetectors having suitable filters so that each photodetector measures a weighted average of light in a range of wavelengths. However, these types of calorimeters typically lack the flexibility to change illuminants and observers as is often required in various industries.

Black/white and color cameras with different Bayer masks have also been used in conjunction with filter wheels to capture spectral images of still items such as paintings. However, cameras with moving filter wheels are often not suitable for analyzing moving objects, such as moving paper sheets (especially with printing or other applied markings).

SUMMARY

This disclosure provides an apparatus and method for camera-based color measurements.

In a first embodiment, a method includes receiving light from a material at a digital imaging device. The method also includes filtering the light into at least three spectral bands using a filter, where different regions of the filter pass different spectral bands. The method further includes measuring the light in each of the spectral bands and determining at least one calorimetric quantity associated with the material using the measured light in the spectral bands.

In particular embodiments, measuring the light in each of the spectral bands includes taking multiple measurements of the light in each of the spectral bands.

In other particular embodiments, the different regions of the filter include multiple masks (where each mask passes one of the spectral bands), different areas of a linear variable filter, and/or individual filters (where each individual filter passes one of the spectral bands).

In yet other particular embodiments, the digital imaging device includes a digital camera. Also, the filter is formed on a detector in the digital camera, and/or a component of the digital camera is replaced with the filter.

In still other particular embodiments, the spectral bands include wavelength bands that are 20 nm in width and that include one or more of the following wavelengths: 350 nm, 400 nm, 450 nm, 500 nm, 550 nm, 600 nm, 650 nm, 700 nm, and 750 nm.

In additional particular embodiments, the method also includes adjusting a process associated with the material based on the at least one determined color. The material could include a paper sheet, and the process could include a paper production process and/or a printing process.

In a second embodiment, an apparatus includes a filter configured to receive light associated with a material and to filter the light into at least three spectral bands, where different regions of the filter pass different spectral bands. The apparatus also includes a detector configured to generate a measurement of the light in each of the spectral bands. In addition, the apparatus includes an interface configured to output the measurements for use in determining at least one calorimetric quantity associated with the material.

In particular embodiments, the detector includes a plurality of pixels each configured to measure the light in one of the spectral bands. In other particular embodiments, the detector includes a charge-coupled device, a complimentary metal oxide semiconductor device, and/or a charge injection device in a digital camera.

In a third embodiment, a system includes an illumination source configured to illuminate a material. The system also includes a color sensor. The color sensor includes a filter configured to receive light associated with the material and to filter the light into at least three spectral bands, where different regions of the filter pass different spectral bands. The color sensor also includes a detector configured to generate measurements of the light in each of the spectral bands. In addition, the color sensor includes an interface configured to output the measurements for use in determining at least one calorimetric quantity associated with the material.

In particular embodiments, the system also includes one or more controllers configured to determine the at least one calorimetric quantity associated with the material and to control a processing or production system based on the at least one determined calorimetric quantity.

In other particular embodiments, the at least one calorimetric quantity includes a spatial calorimetric quantity based on an image of the material and/or an average color of the material.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 4, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
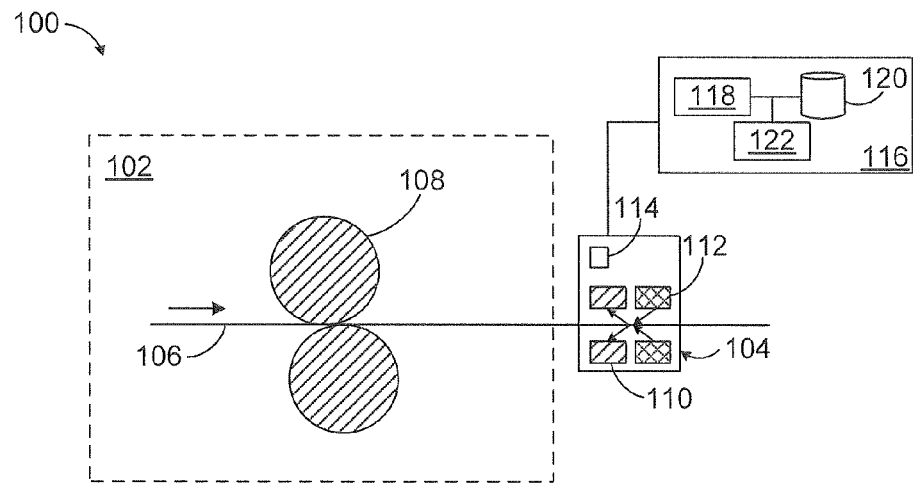
FIG. 1 illustrates an example color measurement system according to this disclosure.

FIG. 1 illustrates an example color measurement system 100 according to this disclosure. The embodiment of the color measurement system 100 shown in FIG. 1 is for illustration only. Other embodiments of the color measurement system 100 could be used without departing from the scope of this disclosure.

In this example, the system 100 generally includes a processing or production system 102 and a color monitor 104. The processing or production system 102 generally denotes any suitable processing or production system that can output at least one item having some form of color to be measured. In this example, the processing or production system 102 is used to produce a paper sheet 106 having some form of color in or on the sheet 106. For example, the processing or production system 102 could represent a paper machine capable of producing a colored paper sheet 106 (including white paper) or a film sheet. The processing or production system 102 could also represent a printing system capable of printing color content onto the paper sheet 106. The processing or production system 102 could represent any other or additional system capable of generating or processing a sheet 106 having at least some form of color or appearance to be measured (such as CIE L*, a*, b* or CIE whiteness). In this example, the processing or production system 102 includes multiple rollers 108, which can be used (among other things) to form the sheet 106 or to impart printing or other colored marks onto the sheet 106. The processing or production system 102 may include any other or additional components depending on the particular function(s) being performed by the system 102. Also, the processing or production system 102 could be used to produce or process any type of item having at least one color to be measured (such as plastic films) and is not limited to use with just paper sheets.

The color monitor 104 is capable of examining one or more items and to measure one or more color or other appearance properties associated with the items. For example, the color monitor 104 could measure the color of the paper sheet 106 or the color of printing placed on the paper sheet 106. In this way, the color monitor 104 can determine whether the processing or production system 102 is producing items with suitable colors, such as colors that satisfy certain color standards or specifications. This may allow the color monitor 104 to ensure that the processing or production system 102 is operating properly and allow identification of potential problems with the processing or production system 102.

In this example, the color monitor 104 includes one or more camera-based color sensors 110. As described in more detail below, each camera-based color sensor 110 includes a detector and a wavelength selectable bandpass filter. The wavelength selectable bandpass filter allows, for example, light within different narrow bandpass ranges to pass to different pixels of the detector. As a result, the detector can measure a broad spectrum of light coming from the sheet 106 or other item being analyzed. Moreover, this can be done very quickly, allowing the camera-based color sensors 110 to be used with still and moving items. As shown in FIG. 1, one or more camera-based color sensors 110 are located on each side of the paper sheet 106. However, this is for illustration only, and one or more camera-based color sensors 110 could be used on a single side of the sheet 106.

The color monitor 104 also includes one or more illumination sources 112. The illumination sources 112 generate light that illuminates the paper sheet 106 or other item being examined. This helps to facilitate more accurate color measurements of the paper sheet 106 or other item. Each of the illumination sources 112 represents any suitable source of light, such as one or more light emitting diodes, bulbs, or other light source(s). The illumination sources 112 could also generate any suitable light, such as white light. Further, any suitable geometry could be used for illuminating the item being examined and for measuring light reflected from or transmitted through the item being examined. In addition, a camera-based color sensor 110 and an associated illumination source 112 could be used on the same side or on different sides of the item being examined.

As shown in FIG. 1, the color monitor 104 may further include a controller 114. The controller 114 could use the measurements from one or more camera-based color sensors 110 to determine the color(s) associated with the sheet 106 or other item. The controller 114 could also use the measurements to determine if the item being examined suffers from various problems, such as when the item has a color that fails to meet specification or has excessive color variations. If problems are found, the controller 114 could take any suitable action, such as notifying an operator or making adjustments to the processing or production system 102. In other embodiments, the controller 114 could collect the measurements from the camera-based color sensors 110 and provide the measurements to an external controller 116, which makes color determinations using the measurements. In yet other embodiments, the measurements from the camera-based color sensors 110 could be provided directly to the external controller 116 without the use of a controller 114 in the color monitor 104. Each of the controllers 114, 116 includes any suitable hardware, software, firmware, or combination thereof for making color determinations using measurements from one or more camera-based color sensors 110. Each of the controllers 114, 116 could, for example, include one or more processors 118 and one or more memories 120 storing instructions and data used, generated, or collected by the processor(s) 118. Each of the controllers 114, 116 could also include one or more network interfaces 122 facilitating communication with external components over a wired or wireless network or communication link.

Although FIG. 1 illustrates one example of a color measurement system 100, various changes may be made to FIG. 1. For example, the system 100 could include any number of processing or production systems 102, color monitors 104, and controllers. Also, FIG. 1 illustrates one example operational environment in which camera-based color measurements can be used. This functionality could be used in any suitable system to measure the color(s) of any suitable item(s).

Figure 2:
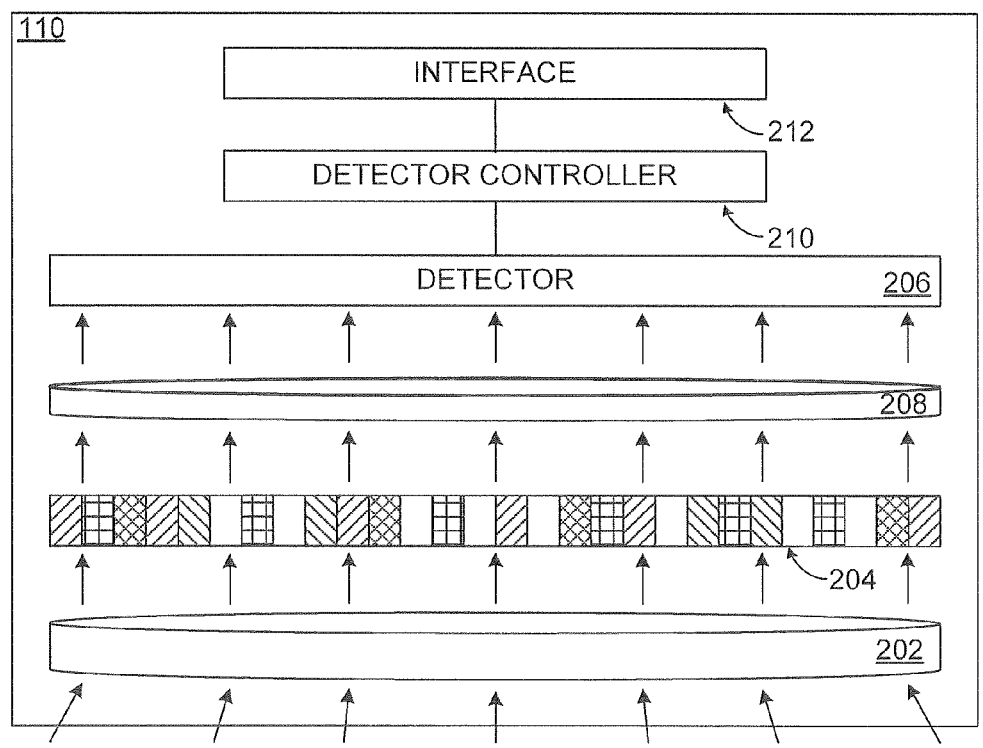
FIG. 2 illustrates an example camera-based color sensor according to this disclosure.

FIG. 2 illustrates an example camera-based color sensor 110 according to this disclosure. The embodiment of the camera-based color sensor 110 shown in FIG. 2 is for illustration only. Other embodiments of the camera-based color sensor 110 could be used without departing from the scope of this disclosure.

As shown in FIG. 2, light transmitted through, reflected from, and/or emitted by a paper sheet 106 or other item being examined can be received at optics 202. The optics 202 alter the light received at the color sensor 110, such as by focusing or diffusing the light. The optics 202 can perform any other or additional functions depending on the implementation. The optics 202 include any suitable structure(s), such as one or more lenses, mirrors, or diffusers.

Light from the item being examined passes through a wavelength selectable bandpass filter 204. The wavelength selectable bandpass filter 204 includes different regions that filter different wavelengths of light. This allows light in different wavelength bands to pass through the different regions of the filter 204. For example, different regions of the wavelength selectable bandpass filter 204 could filter the light into different bands that are 20 nanometers wide. As particular examples, regions in the wavelength selectable bandpass filter 204 could filter light into different 20 nanometer-wide bands centered at or including 350 nm, 400 nm, 450 nm, 500 nm, 550 nm, 600 nm, 650 nm, 700 nm, and 750 nm. The wavelength selectable bandpass filter 204 includes any suitable structure(s) for filtering light into different wavelength bands. Example embodiments of the wavelength selectable bandpass filter 204 are shown in FIGS. 3A through 3F, which are described below.

The filtered wavelength bands are received at a detector 206. The detector 206 is capable of measuring an intensity of light in the various wavelength bands provided by the wavelength selectable bandpass filter 204. For example, the detector 206 could include an array or matrix of smaller detectors, such as an array or matrix of pixels. Each detector in the array or matrix could be used to measure the intensity of light provided in one of the wavelength bands. By using multiple detectors to measure light in multiple wavelength bands, spectral or calorimetric information about the item being examined can be obtained, allowing the color(s) of the item to be determined. For instance, multiple detectors in the array or matrix could simultaneously measure light in multiple wavelength bands, thereby enabling the use of the color sensor 110 with a moving item. The detector 110 includes any suitable structure(s) for measuring light in multiple wavelength bands. The detector 110 could, for example, represent a charge-coupled device (CCD), a complimentary metal oxide semiconductor (CMOS) device, or a charge injection device (CID).

Micro-optics 208 could be used to focus light from the wavelength selectable bandpass filter 204 onto individual pixels or other structures of the detector 206. The micro-optics 208 include any suitable structure(s), such as microlenses formed on the surface of the detector 206.

A detector controller 210 is coupled to and controls the operation of the detector 206. For example, the detector controller 210 could cause the detector 206 to begin measuring light and to stop measuring light in wavelength bands provided by the wavelength selectable bandpass filter 204. The detector controller 210 could also receive measurement data from the detector 206 and provide the measurement data to an external component, such as the controller 114 or 116. The detector controller 210 could perform any other or additional actions to facilitate operation of the detector 206. The detector controller 210 includes any suitable structure(s) for controlling the operation of one or more detectors.

An interface 212 can be used to facilitate communication between the color sensor 110 and an external component, such as the controller 114 or 116. The interface 212 could support communications over any suitable type of communication medium, such as a wired or wireless network or link. The interface 212 includes any suitable structure supporting communication with the color sensor 110. As particular examples, the interface 212 could support communications over a Universal Serial Bus (USB) link, a FireWire link, or a gigabit Ethernet link.

In some embodiments, the entire color sensor 110 could be implemented using a digital camera or other digital imaging device. In general, a "digital imaging device" represents any digital device designed to capture visual information using individual pixels or other image capturing elements. In these embodiments, a custom filter (the wavelength selectable bandpass filter 204) can be used in front of the camera's pixels or other image capturing elements (the detector 206) to enable the camera to be utilized as a color analyzer/sensor. Conventional digital cameras typically use red-green-blue (RGB) or cyan-magenta-yellow (CMY) filters, which are inappropriate for calorimetric measurements. The wavelength selectable bandpass filter 204 provides proper wavelength bands for spectral analysis and color determinations. In particular embodiments, at least four wavelength bands are provided by the wavelength selectable bandpass filter 204 for detection and analysis, although any other suitable number of wavelength bands could be used. The wavelength bands could represent any suitable wavelength bands, whether in the ultraviolet, visible, near infrared, infrared, or other spectrums.

Digital cameras may be less expensive than other color measurement techniques, such as those using expensive diffraction grating-based spectrometers. Also, the wavelength selectable bandpass filter 204 could be removable, allowing different wavelength selectable bandpass filters 204 to be inserted into and used in the color sensor 110. This would allow the same overall color sensor structure to be reused for various types of measurements, further reducing costs to users of the color sensors. Further, since narrow wavelength bands are measured in the color sensor 110, the color sensor 110 could reduce signal-to-noise ratios in the color measurements (such as by examining larger areas of the sheet 106 and averaging spatial pixel values). In addition, the color sensor 110 could be smaller than conventional color measuring devices, enabling the color sensor 110 to be used in space-confined applications.

In particular embodiments, a digital camera could be fabricated with the wavelength selectable bandpass filter 204. For example, the wavelength selectable bandpass filter 204 could be formed as part of the detector 206, such as during formation of a CCD, CMOS, or CID-based detector 206. In other particular embodiments, the wavelength selectable bandpass filter 204 could be retrofitted into an existing digital camera. For instance, the cover glass or infrared block on a digital camera could be replaced with the wavelength selectable bandpass filter 204. A digital camera incorporating the wavelength selectable bandpass filter 204 could be produced in any other suitable manner.

In some embodiments, the detector 206 can be calibrated to ensure proper operation of the color sensor 110. A photometric calibration could occur in any suitable manner, such as by using a calibration tile. The calibration tile could include different areas with known reflectances at specific wavelength bands. The calibration tile could be illuminated (such as by using an illumination source 112), and measurements of the calibration tile could be taken using the detector 206. In this way, a controller or other component can determine how the detector 206 operates given specific illumination of a surface with known reflectances. Also, a wavelength calibration could occur in any suitable manner, such as by using a mercury pen-ray lamp and/or wavelength calibration tiles. These types of calibrations are generally well known to one skilled in the art.

Although FIG. 2 illustrates one example of a camera-based color sensor 110, various changes may be made to FIG. 2. For example, the color sensor 110 may or may not require optics 202, 208. Also, various embodiments of the wavelength selectable bandpass filter 204 could be used, and the different filtering regions of the wavelength selectable bandpass filter 204 may be arranged in a pattern or arranged randomly or pseudo-randomly.

FIGS. 3A through 3F illustrate example wavelength selectable bandpass filters 204 for use in a camera-based color sensor 110 according to this disclosure. The embodiments of the wavelength selectable bandpass filters shown in FIGS. 3A through 3F are for illustration only. Other embodiments of the wavelength selectable bandpass filter could be used without departing from the scope of this disclosure.

Figure 3A:
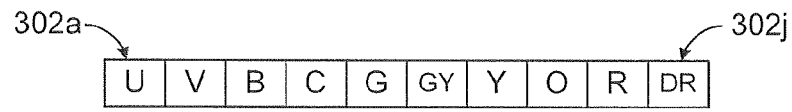
FIGS. 3A through 3F illustrate example wavelength selectable bandpass filters for use in a camera-based color sensor according to this disclosure.

As shown in FIG. 3A, a wavelength selectable bandpass filter includes a single row of pixel masks 302a-302j, each of which is designed to pass a different wavelength band of light. For example, the pixel masks 302a-302j could be respectively designed to pass light in the following bands of the spectrum: ultraviolet (U) violet (V), blue (B), cyan (C), green (G), green-yellow (GY), yellow (Y), orange (O), red (R), and deep red (DR). Each of these pixel masks 302a-302j can filter light passing through it so that only light falling into one of these wavelength bands is passed. Various pixels or other detectors could then be used to measure the intensity of light in each of the wavelength bands, allowing the color of an item to be determined. In this example, each of the pixel masks 302a-302j is aligned with a single pixel or other detector. Also, while shown as a single row of pixel masks 302a-302j, this row could be replicated any number of times (whether the order of the pixel masks 302a-302j in the rows remains the same or changes).

Figure 3B:
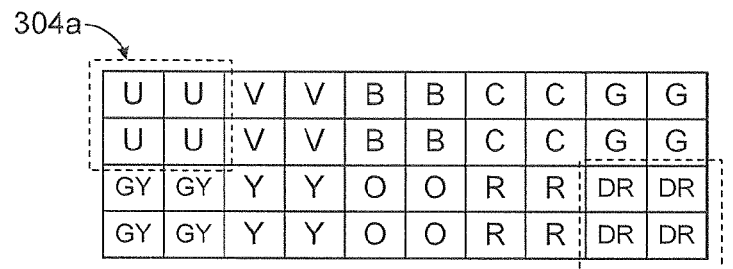

As shown in FIG. 3B, a wavelength selectable bandpass filter includes blocks 304a-304j of pixel masks, each block representing a 2×2 block of pixel masks. The blocks 304a-304j are designed to pass different wavelength bands to multiple sets of pixels or other detectors (in this case, four pixels per block). This allows multiple measurements to be taken of light passing through each of the blocks 304a-304j, which may allow, for example, an average measurement value to be determined for each of the wavelength bands. Again, the structure in FIG. 3B could be replicated any number of times (whether the order of the pixel blocks 304a-304j remains the same or changes).

Figure 3C:
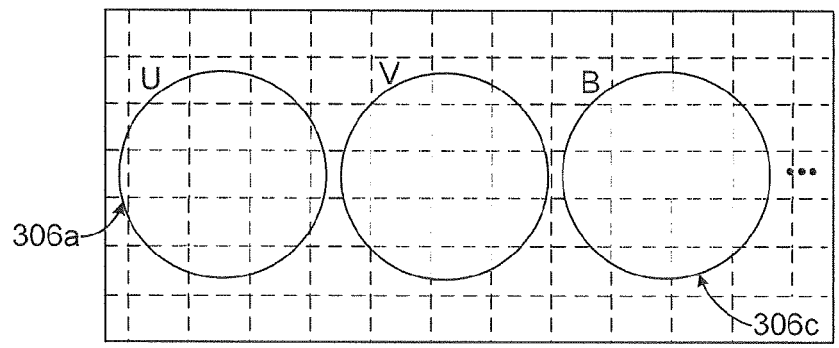

As shown in FIG. 3C, a wavelength selectable bandpass filter includes discrete masks 306a-306c. The discrete masks 306a-306c are designed to pass different wavelength bands to pixels or other detectors. In this example, the masks 306a-306c are not aligned with pixels or other individual detectors (the pixels are denoted with dashed lines), and light from each of the masks 306a-306c may fall completely or partially on a pixel. The pixels partially receiving light may or may not be used to generate measurement data. While only three discrete masks are shown in FIG. 3C, other discrete masks could be used for the other wavelength ranges described above. Also, multiple masks could be used for each wavelength band.

Figure 3D:
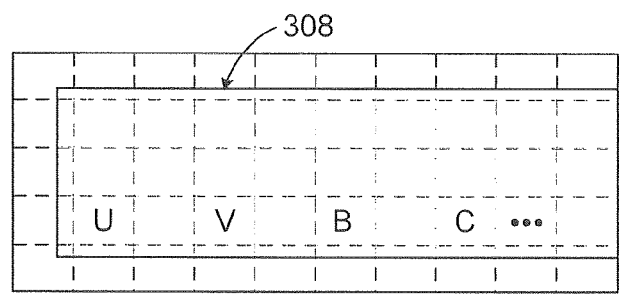

As shown in FIG. 3D, a wavelength selectable bandpass filter includes a linear variable filter 308, which can be placed over a number of pixels or other detectors. The linear variable filter 308 generally transitions in its filtering function, allowing light in one wavelength band to pass in one area of the filter 308 and allowing light in another wavelength band to pass in a different area of the filter 308. Although not shown, the linear variable filter 308 could transition and allow light to pass in all of the wavelength bands noted above. Also, one or multiple linear variable filters 308 could be used. In some embodiments, a linear variable filter 308 could be formed by applying a suitable coating on the surface of the detector 206 or on the surface of a glass cover of the detector 206. In particular embodiments, a linear variable filter 308 could be limited to use with visible light, and additional structures could be used to allow other narrow bands of light to pass (such as near infrared and infrared bands). For example, a glass doped with Holmium or Neodymium could be used to pass particular known groups of narrow wavelength bands for wavelength calibration or other purposes.

Figure 3E:
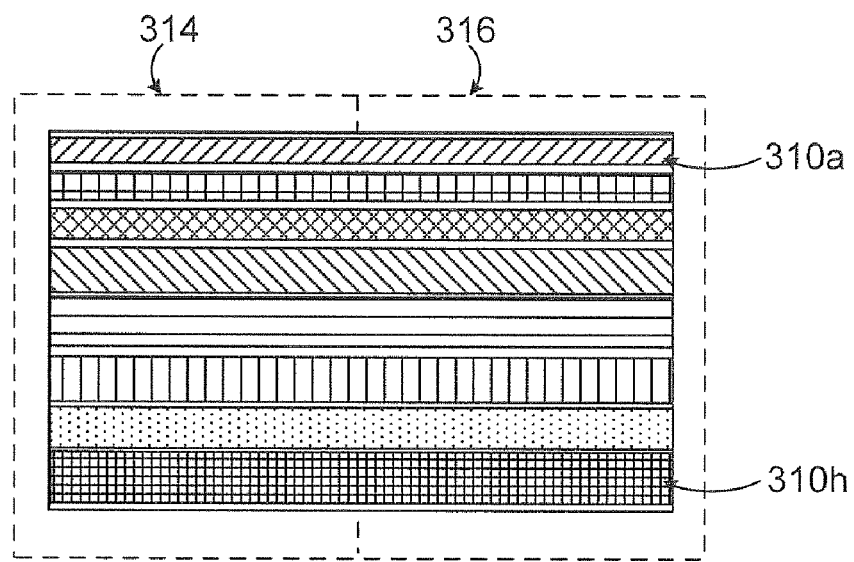

In FIG. 3E, a wavelength selectable bandpass filter includes multiple filters or regions 310a-310h, each of which may be aligned with or otherwise associated with one or multiple rows of pixels or other detectors. Each one of these regions 310a-310h could pass a different wavelength band of light, such as one of the wavelength bands discussed above. The regions 310a-310h could have any suitable size and shape, and the regions 310a-310h may or may not have the same size or shape.

Figure 3F:
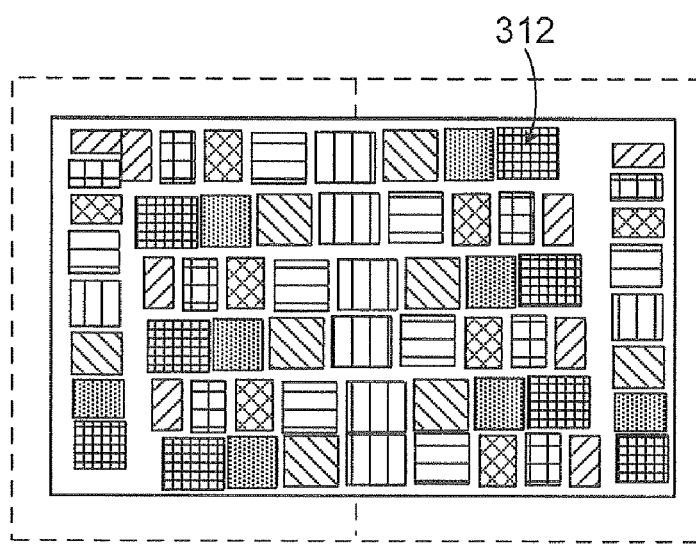

In FIG. 3F, a wavelength selectable bandpass filter includes multiple filters or regions 312, each of which may be aligned or otherwise associated with one or multiple pixels or other individual detectors. Each of these regions 312 could pass a different wavelength band of light, such as one of the wavelength bands discussed above. The regions 312 could have any suitable size and shape, and the regions 312 may or may not have the same size or shape. The arrangement of the regions 312 could be periodic, random, or pseudo-random.

In these various embodiments, the wavelength selectable bandpass filter is used to allow light in different narrow wavelength bands to reach different pixels or other portions of the detector 206. This allows the detector 206 to measure the spectrum of light coming from the item being examined. The wavelength bands passed by the wavelength selectable bandpass filter could represent any suitable bands, such as different 20 nanometer-wide bands centered at or including 350 nm, 400 nm, 450 nm, 500 nm, 550 nm, 600 nm, 650 nm, 700 nm, and 750 nm. However, any other or additional wavelength bands could be provided by the wavelength selectable bandpass filter and measured by the detector 206. Also, areas of pixels or other individual detectors within the detector 206 could be predefined prior to use, where the areas of pixels or other detectors correspond to the different filtering regions of the wavelength selectable bandpass filter 204.

In some embodiments, the signal-to-noise ratios in the wavelength bands passed from the wavelength selectable bandpass filter could be similar or equal. Also, the sensitivity of the detector 206 may or may not be the same at all wavelength bands. Further, the transmittance of the wavelength selectable bandpass filter may or may not vary as a function of wavelength. Beyond that, the total area of the wavelength selectable bandpass filter used to provide light at a particular wavelength band could be selected in any suitable manner, such as to optimize the signal-to-noise ratio for that wavelength band. In addition, the pattern of the regions used to provide light at particular wavelength bands could be selected based on any suitable criteria, such as the measurement task to be performed. In other embodiments, multiple bandpass filters may be provided, not all of which are simultaneously deployed in front of the detector. In these embodiments, the bandpass filter or set of filters deployed at any time can be selected according to the measurement task to be performed.

As shown in FIGS. 3E and 3F, in some embodiments, the wavelength selectable bandpass filter could be used in conjunction with one or more backings 314-316. For example, a paper sheet 106 or other item could be placed on the top of the backings 314-316 (between the backings and the wavelength selectable bandpass filter). The paper sheet 106 or other item could be illuminated, and the wavelength selectable bandpass filter could then filter light reflected from the paper sheet 106 or other item over the backings 314-316. In this way, color measurements associated with multiple backings can be captured at the same time. In particular embodiments, the backings 314-316 represent white and black backings, and color measurements taken using these backings 314-316 could be used to predict the color of the paper sheet 106 or other item with any other backing. The use of two backings is for illustration only. Any number of backings could be used here, such as when black and white (or other color) backings are arranged in a checkerboard pattern. Also, backings could be used with any of the wavelength selectable bandpass filters shown here or with other wavelength selectable bandpass filters.

As noted above, different types of optics can be used in the color sensor 110, and the use of optics in the color sensor 110 may be optional. If a defocused image of a paper sheet 106 or other item is received at the wavelength selectable bandpass filter, the light in the defocused image could represent the average light from the paper sheet 106 or other item (or a portion thereof). In this case, each filtering region of the wavelength selectable bandpass filter could output the portion of that average light falling within the narrow wavelength band of that region. The measured values produced by the detector 206 could then be used in any suitable manner, such as by summing the measurements for each individual wavelength band to produce improved measurement values.

If a focused image of the paper sheet 106 or other item is received at the wavelength selectable bandpass filter, the light in the image can vary depending on the color of the item in different areas of the focused image. In this case, at least some of the filtering regions of the wavelength selectable bandpass filter could receive light from different areas of the paper sheet 106 or other item. The filtering regions of the wavelength selectable bandpass filter could therefore output light in narrow wavelength bands from different areas of the paper sheet 106 or other item. In this way, the detector 206 could be used, for example, to detect color variations in different areas of the paper sheet 106 or other item. For measurements with different spatial resolutions, corresponding patterns of regions on the bandpass filter and suitable degrees of focusing sharpness (or de-focusing) can be chosen and used.

Although FIGS. 3A through 3F illustrate examples of wavelength selectable bandpass filters 204 for use in a camera-based color sensor 110, various changes may be made to FIGS. 3A through 3F. For example, a wavelength selectable bandpass filter 204 could include any suitable number of regions passing different wavelength bands, such as regions passing at least four different spectral bands. Also, each of the regions of the wavelength selectable bandpass filter 204 could have any suitable size and shape, and the regions could have any suitable arrangement. Furthermore, some of the regions of the bandpass filter may pass essentially all wavelength bands. In addition, the use of the backings 314-316 may or may not be needed, depending on the implementation.

Figure 4:
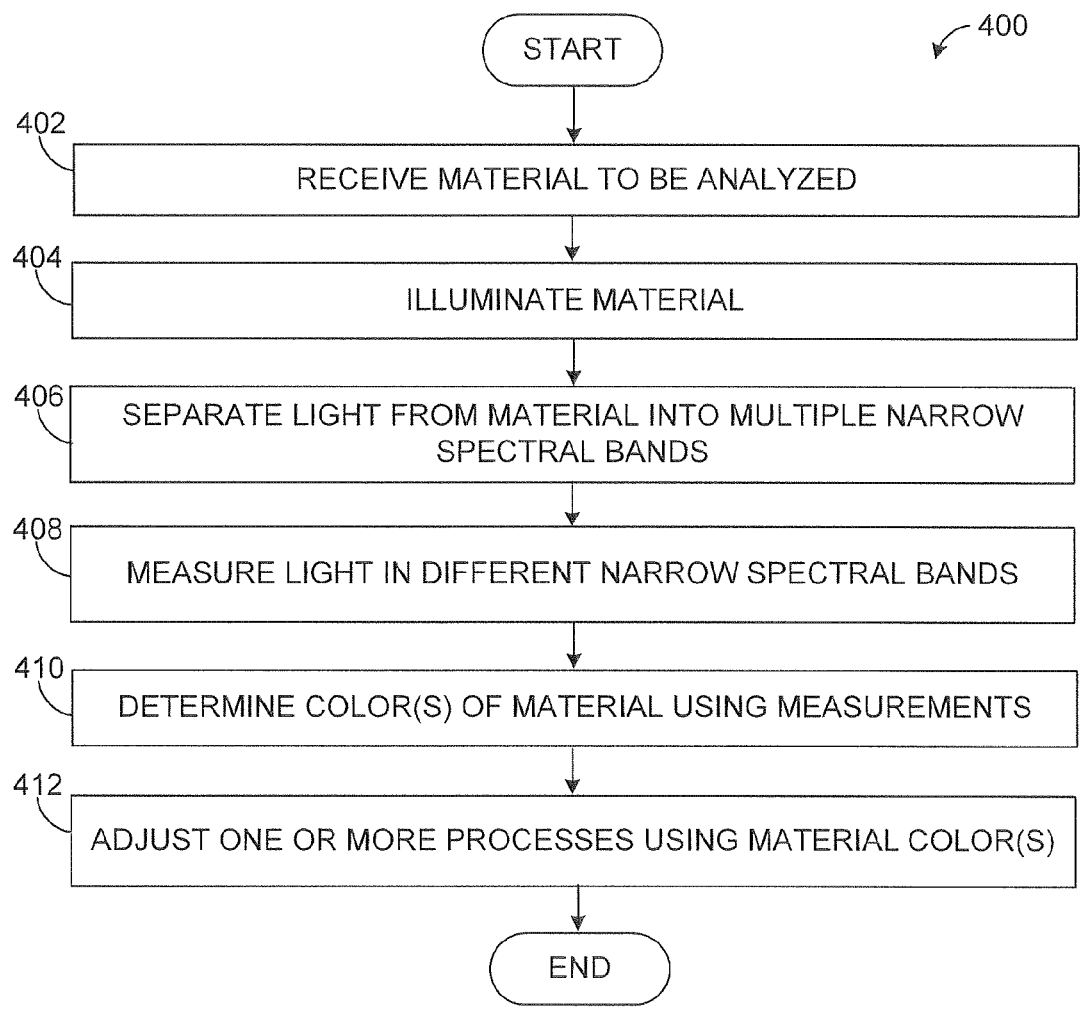
FIG. 4 illustrates an example method for camera-based color measurements according to this disclosure.

FIG. 4 illustrates an example method 400 for camera-based color measurements according to this disclosure. The embodiment of the method 400 shown in FIG. 4 is for illustration only. Other embodiments of the method 400 could be used without departing from the scope of this disclosure.

A material to be analyzed is received at step 402. This may include, for example, placing a color monitor 104 near the surface of a still or moving item (or placing a still or moving item near the color monitor 104). As a particular example, this may include running a paper sheet 106 being formed or processed past the color monitor 104.

The material is illuminated at step 404. This may include, for example, using one or more illumination sources 112 to illuminate one or more surfaces of the material. As a particular example, this may include using one or more illumination sources 112 to illuminate one or more surfaces of the paper sheet 106. Any suitable light could be used here, such as white light. Illumination sources 112 could be used so that one or more spectral power distributions are used to irradiate the surface of the material, allowing one or more measurement to be utilized to form a final calorimetric quantity.

Light from the material is separated into multiple narrow spectral bands at step 406. This may include, for example, passing light reflected from or transmitted by the material through a wavelength selectable bandpass filter 204. The wavelength selectable bandpass filter 204 includes multiple regions, each of which can block all light except for light in narrow spectral bands. The wavelength selectable bandpass filter 204 may include at least one region for each of the narrow spectral bands to be analyzed.

The light in the narrow spectral bands is measured at step 408. This may include, for example, measuring the intensity of the light in each of the narrow spectral bands using one or more pixels in the detector 206. Any suitable number of pixels could be used to measure the light in each of the narrow spectral bands.

One or more colors of the material are determined at step 410. This may include, for example, the detector 206 outputting the measured values of light in each of the narrow spectral bands. This may also include the controller 114, 116 using the measured values to determine one or more colors associated with the material being analyzed. The measured color(s) could then be used in any suitable manner. For example, the measured color(s) may be used to adjust one or more processes at step 412. This could include, for example, altering one or more processes performed in the processing or production system 102. These alterations could be made to improve color uniformity or reduce color variation. These alterations could also be made to ensure that an item satisfies desired or required color specifications. The measured color(s) could be used in any other suitable manner.

Although FIG. 4 illustrates one example of a method 400 for camera-based color measurements, various changes may be made to FIG. 4. For example, while shown as a series of steps, various steps in FIG. 4 could overlap, occur in parallel, or occur multiple times.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   disposing a material between a filter and a plurality of backings, each backing comprising a different color;
   receiving light from a plurality of sections of the material at a digital imaging device, each section disposed over a different one of the backings, the light comprising a defocused image of the material, the light in the defocused image comprising an average light from the material;
   filtering the light into at least three spectral bands using the filter, wherein different regions of the filter pass different spectral bands, the different regions of the filter arranged in a matrix having a plurality of rows and a plurality of columns;
   measuring the light in each of the spectral bands, wherein the light in each spectral band comprises a portion of the average light from the material falling within that spectral band; and
   determining at least one colorimetric quantity associated with the material using the measured light in the spectral bands, the at least one colorimetric quantity comprising at least one CIE value.

2. The method of claim 1, wherein measuring the light in each of the spectral bands comprises taking multiple measurements of the light in each of the spectral bands.

3. The method of claim 1, wherein the different regions of the filter comprise multiple masks, each of the masks passing one of the spectral bands.

4. The method of claim 1, wherein the different regions of the filter comprise different areas of a linear variable filter.

5. The method of claim 1, wherein each of the spectral bands has a width of approximately 20 nm.

6. The method of claim 1, wherein the digital imaging device comprises a digital camera, the filter formed on a detector in the digital camera.

7. The method of claim 1, wherein at least one of the spectral bands includes at least one of: ultraviolet wavelengths and infrared wavelengths.

8. The method of claim 1, wherein the spectral bands comprise wavelength bands that are 20 nm in width and that include one or more of: 350 nm, 400 nm, 450 nm, 500 nm, 550 nm, 600 nm, 650 nm, 700 nm, and 750 nm.

9. The method of claim 1, further comprising:
   adjusting a process associated with the material based on the at least one determined colorimetric quantity.

10. The method of claim 9, wherein:
    the material comprises a still or moving sheet; and
    the process comprises one or more of: a paper production process, a plastic production process, and a paper or textile printing process.

11. An apparatus comprising:
    a filter configured to receive light associated with a plurality of sections of a material and to filter the light into at least three spectral bands, different regions of the filter configured to pass different spectral bands, the different regions of the filter arranged in a matrix having a plurality of rows and a plurality of columns;
    a plurality of backings disposed on a side of the material opposite the filter, each backing comprising a different color, each backing associated with a different one of the sections of the material;
    a detector configured to generate a measurement of the light in each of the spectral bands;
    and an interface configured to output the measurements for use in determining at least one colorimetric quantity associated with the material, the at least one colorimetric quantity comprising at least one CIE value;
    wherein the filter is configured to receive light comprising a defocused image of the material, the light in the defocused image comprising an average light from the material; and
    wherein the detector is configured to measure the light in each of the spectral bands, wherein the light in each spectral band comprises a portion of the average light from the material falling within that spectral band.

12. The apparatus of claim 11, wherein the detector is configured to generate multiple measurements of the light in each of the spectral bands.

13. The apparatus of claim 11, wherein the different regions of the filter comprise multiple masks, each of the masks passing one of the spectral bands.

14. The apparatus of claim 11, wherein the different regions of the filter comprise different areas of a linear variable filter.

15. The apparatus of claim 11, wherein each of the spectral bands has a width of approximately 20 nm.

16. The apparatus of claim 11, wherein the detector comprises a plurality of pixels each configured to measure the light in one of the spectral bands.

17. The apparatus of claim 11, wherein the detector comprises at least one of: a charge-coupled device, a complimentary metal oxide semiconductor device, and a charge injection device in a digital camera.

18. The apparatus of claim 11, wherein the filter is disposed on a surface of the detector.

19. A system comprising:
    an illumination source configured to illuminate a material having a plurality of sections;
    a plurality of backings disposed in proximity of a first side of the material, each backing comprising a different color, each backing associated with a different one of the sections of the material; and
    a color sensor comprising:
      a filter disposed on a second side of the material opposite the first side, the filter configured to receive light associated with each of the sections of the material and to filter the light into at least three spectral bands, different regions of the filter configured to pass different spectral bands, the different regions of the filter arranged in a matrix having a plurality of rows and a plurality of columns;
      a detector configured to generate a measurement of the light in each of the spectral bands; and
      an interface configured to output the measurements for use in determining at least one colorimetric quantity associated with the material, the at least one colorimetric quantity comprising at least one CIE value;
    wherein the filter is configured to receive light comprising a defocused image of the material, the light in the defocused image comprising an average light from the material; and
    wherein the detector is configured to measure the light in each of the spectral bands, wherein the light in each spectral band comprises a portion of the average light from the material falling within that spectral band.

20. The system of claim 19, further comprising:
    one or more controllers configured to determine the at least one colorimetric quantity associated with the material and to control a processing or production system based on the at least one determined colorimetric quantity.

21. The system of claim 19, wherein the color sensor further comprises a plurality of micro-lenses configured to focus light from the filter onto individual pixels of the detector.

22. The system of claim 19, wherein the different regions of the filter comprise multiple masks, each of the masks passing one of the spectral bands.

* * * * *